(12) United States Patent
Mitelberg et al.

(10) Patent No.: US 6,960,228 B2
(45) Date of Patent: *Nov. 1, 2005

(54) INTRAVASCULAR STENT DEVICE

(75) Inventors: Vladimir Mitelberg, Aventura, FL (US); Donald K. Jones, Lauderhill, FL (US)

(73) Assignee: Cordis Neurovascular, Inc., Miami Lake, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/722,336

(22) Filed: Nov. 25, 2003

(65) Prior Publication Data
US 2004/0158306 A1 Aug. 12, 2004

Related U.S. Application Data

(62) Division of application No. 10/163,116, filed on Jun. 5, 2002, now Pat. No. 6,673,106.
(60) Provisional application No. 60/298,326, filed on Jun. 14, 2001.

(51) Int. Cl.[7] .................................................. A61F 2/06
(52) U.S. Cl. ...................................... 623/1.2; 623/1.15
(58) Field of Search ............................. 623/1.15, 1.16, 623/1.17–1.22

(56) References Cited

U.S. PATENT DOCUMENTS

| 4,443,498 A | 4/1984 | Shinno |
| 4,512,338 A | 4/1985 | Balko et al. |
| 4,665,906 A | 5/1987 | Jervis |

(Continued)

FOREIGN PATENT DOCUMENTS

| EP | 0 547 530 B1 | 6/1993 |
| EP | 0 664 104 B1 | 7/1995 |
| EP | 1 000 590 A1 | 5/2000 |
| EP | 1 042 997 A1 | 10/2000 |
| EP | 1 157 673 A2 | 11/2001 |
| EP | 1 266 639 A2 | 12/2002 |
| WO | WO 97/25000 | 7/1997 |
| WO | WO 97/26840 | 7/1997 |
| WO | WO 98/32412 | 7/1998 |
| WO | WO 02/054980 A2 | 7/2002 |

OTHER PUBLICATIONS

U.S. Appl. No. 10/163,248, Mitelberg et al.
U.S. Appl. No. 10/743,510, Mitelberg et al.

*Primary Examiner*—Corrine McDermott
*Assistant Examiner*—Hieu Phan

(57) ABSTRACT

A very small diameter intravascular stent device which may be used to occlude or partially occlude an aneurysm in the human brain, the stent device includes a thin-walled skeletal cylindrical tube fonned of S-shaped, or sinusoidal, elements which, when compressed, nest tightly with each other.

8 Claims, 2 Drawing Sheets

U.S. PATENT DOCUMENTS

| | | |
|---|---|---|
| 4,733,665 A | 3/1988 | Palmaz |
| 4,739,762 A | 4/1988 | Palmaz |
| 4,739,768 A | 4/1988 | Engelson |
| 4,776,337 A | 10/1988 | Palmaz |
| 4,796,629 A | 1/1989 | Grayzel |
| 4,878,906 A | 11/1989 | Lindemann et al. |
| 4,994,069 A | 2/1991 | Ritchart et al. |
| 4,994,071 A | 2/1991 | MacGregor |
| 5,102,417 A | 4/1992 | Palmaz |
| 5,108,407 A | 4/1992 | Geremia et al. |
| 5,122,136 A | 6/1992 | Guglielmi et al. |
| 5,195,970 A | 3/1993 | Gahara |
| 5,226,887 A | 7/1993 | Farr et al. |
| 5,226,911 A | 7/1993 | Chee et al. |
| 5,261,916 A | 11/1993 | Engelson |
| 5,288,711 A | 2/1994 | Mitchell et al. |
| 5,316,023 A | 5/1994 | Palmaz et al. |
| 5,342,348 A | 8/1994 | Kaplan |
| 5,354,294 A | 10/1994 | Chou |
| 5,354,295 A | 10/1994 | Guglielmi et al. |
| 5,360,443 A | 11/1994 | Barone et al. |
| 5,378,239 A | 1/1995 | Termin et al. |
| 5,514,176 A | 5/1996 | Bosley, Jr. |
| 5,516,781 A | 5/1996 | Morris et al. |
| 5,522,836 A | 6/1996 | Palermo |
| 5,522,880 A | 6/1996 | Barone et al. |
| 5,551,954 A | 9/1996 | Buscemi et al. |
| 5,563,146 A | 10/1996 | Morris et al. |
| 5,565,036 A | 10/1996 | Westendorp et al. |
| 5,569,245 A | 10/1996 | Guglielmi et al. |
| 5,571,170 A | 11/1996 | Palmaz et al. |
| 5,571,171 A | 11/1996 | Barone et al. |
| 5,578,071 A | 11/1996 | Parodi |
| 5,578,072 A | 11/1996 | Barone et al. |
| 5,591,195 A | 1/1997 | Taheri et al. |
| 5,607,466 A | 3/1997 | Imbert et al. |
| 5,609,628 A | 3/1997 | Keranen |
| 5,646,160 A | 7/1997 | Morris et al. |
| 5,656,023 A | 8/1997 | Caprio, Jr. et al. |
| 5,656,036 A | 8/1997 | Palmaz |
| 5,665,728 A | 9/1997 | Morris et al. |
| 5,683,453 A | 11/1997 | Palmaz |
| 5,725,572 A | 3/1998 | Lam et al. |
| 5,735,893 A | 4/1998 | Lau et al. |
| 5,741,327 A | 4/1998 | Frantzen |
| 5,772,668 A | 6/1998 | Summers et al. |
| 5,800,520 A | 9/1998 | Fogarty et al. |
| 5,807,404 A | 9/1998 | Richter |
| 5,810,872 A | 9/1998 | Kanesaka et al. |
| 5,827,321 A | 10/1998 | Roubin et al. |
| 5,855,600 A | 1/1999 | Alt |
| 5,931,867 A | 8/1999 | Haindl |
| 5,980,514 A | 11/1999 | Kupiecki et al. |
| 6,004,347 A | 12/1999 | McNamara et al. |
| 6,042,597 A | 3/2000 | Kveen et al. |
| 6,083,257 A | 7/2000 | Taylor et al. |
| 6,096,034 A | 8/2000 | Kupiecki et al. |
| 6,106,548 A | 8/2000 | Roubin et al. |
| 6,117,165 A | 9/2000 | Becker |
| 6,152,957 A | 11/2000 | Jang |
| 6,168,592 B1 | 1/2001 | Kupiecki et al. |
| 6,179,868 B1 | 1/2001 | Burpee et al. |
| 6,193,747 B1 | 2/2001 | von Oepen |
| 6,254,612 B1 | 7/2001 | Hieshima |
| 6,261,319 B1 | 7/2001 | Kveen et al. |
| 6,267,783 B1 | 7/2001 | Letendre et al. |
| 6,287,366 B1 | 9/2001 | Derive et al. |
| 6,344,041 B1 | 2/2002 | Kupiecki et al. |
| 6,361,558 B1 | 3/2002 | Hieshima et al. |
| 6,673,106 B2 * | 1/2004 | Mitelberg et al. ............ 623/1.2 |
| 6,712,843 B2 * | 3/2004 | Elliott ....................... 623/1.15 |
| 6,749,628 B1 * | 6/2004 | Callol et al. ............... 623/1.15 |
| 2003/0004567 A1 | 1/2003 | Boyle et al. |
| 2003/0216807 A1 | 11/2003 | Jones et al. |
| 2004/0068314 A1 | 4/2004 | Jones et al. |

* cited by examiner

INTRAVASCULAR STENT DEVICE

CROSS-REFERENCE TO RELATED APPLICATION

This patent application is a divisional patent application of U.S. patent application Ser. No. 10/163,116, filed on Jun. 5, 2002, entitled, "Intravascular Stent Device," now U.S. Pat. No. 6,673,106, which is a nonprovisional patent application of U.S. provisional patent application Ser. No. 60/298,326, filed on Jun. 14, 2001, entitled, "Intravascular Stent."

BACKGROUND OF THE INVENTION

1. Field of the Invention

This invention relates to intravascular devices for implantation within a vessel of the body, and more particularly to a stent device which may be used in the treatment of blood vessel disorders. More specifically, the intravascular device may take the form of an aneurysm cover to be used in the treatment of aneurysms which occur in the brain.

2. Description of the Prior Art

On a worldwide basis, nearly one million balloon angioplasties were performed in 1997 to treat vascular disease, including blood vessels clogged or narrowed by a lesion or stenosis. The objective of this procedure is to increase the inner diameter or cross-sectional area of the vessel passage, or lumen, through which blood flows.

Another serious vascular defect is an area of weakened vessel wall that causes a bulge, or bubble, to protrude out in a radial direction from the vessel. This type of defect is called an aneurysm. If untreated, the aneurysm may continue expanding until it bursts thereby causing hemorrhaging from the vessel.

In an effort to prevent restenosis or treat an aneurysm without requiring surgery, short flexible cylinders or scaffolds, made of metal or polymers, are often placed into a vessel to maintain or improve blood flow. Referred to as stents, various types of these devices are widely used for reinforcing diseased blood vessels, for opening occluded blood vessels, and for defining an internal lumen to relieve pressure in an aneurysm. The stents allow blood to flow through the vessels at an improved rate while providing the desired lumen opening or structural integrity lost by the damaged vessels. Some stents are expanded to the proper size by inflating a balloon catheter, referred to as "balloon expandable" stents, while others are designed to elastically resist compression in a "self-expanding" manner.

Balloon expandable stents and self-expanding stents are generally delivered in a cylindrical form, crimped to a smaller diameter and are placed within a vessel using a catheter-based delivery system. When positioned at a desired site within a vessel, these devices are expanded by a balloon, or allowed to "self-expand," to the desired diameter.

One such stent for treatment of abdominal aortic aneurysms is disclosed in U.S. Pat. No. 6,267,783 to Robert P. Letendre, et al. This patent discloses a self-expanding stent which may be used in the treatment of aortic aneurysms. This device may be easily recaptured after placement and repositioned to a new position within the vessel. This patent, assigned to a related company, is subsequently referred to and the disclosure therein is incorporated and made a part of the subject patent application.

Another stent aneurysm treatment device is disclosed in U.S. Pat. No. 6,361,558, assigned to the same assignee as the present application. This patent discloses vasculature stents of various configurations which may be used as aneurysm covers for occluding, or partially occluding, aneurysms located at various positions along the blood vessels.

SUMMARY OF THE INVENTION

There is a need for an improved stent which may be easily delivered to a vasculature site through a very small catheter, is capable of being repositioned and which exhibits sufficient structural integrity and resilience under radial compressive forces. More particularly, there is a need for such a stent that, in its compressed state prior to delivery of the stent, has a diameter which is extremely small. Such a stent could be placed in a very small microcatheter for subsequent positioning within a vessel of the human brain. Obviously, such vessels are extremely small and very tortuous throughout their length.

In accordance with one aspect of the present invention, there is provided a self-expanding stent which includes a small diameter skeletal tubular member. The skeletal tubular member is comprised of a plurality of cells which are formed by a plurality of interconnected, non-inverted horizontal and inverted horizontal S-shaped members. The S-shaped members are generally parallel to the longitudinal axis of the tubular member and are interconnected in a repeating pattern. Each of the S-shaped members has a proximal end, a distal end, a proximal intermediate section and a distal intermediate section. The proximal end of each non-inverted horizontal S-shaped member is attached to the distal intermediate section of an adjacent inverted horizontal S-shaped member, the distal end of each non-inverted horizontal S-shaped member is attached to the proximal intermediate section of another adjacent inverted horizontal S-shaped member, the proximal end of each inverted horizontal S-shaped member is attached to the distal intermediate section of an adjacent non-inverted horizontal S-shaped member, and the distal end of each inverted horizontal S-shaped member is attached to said proximal intermediate section of another adjacent non-inverted horizontal S-shaped member. With this configuration, the skeletal tubular member may be compressed to a very small diameter because of "nesting" of adjacent S-shaped members.

In accordance with another aspect of the present invention, as the skeletal tubular member is compressed into a small diameter, each proximal intermediate section of each non-inverted horizontal S-shaped member pulls on a distal end of an adjacent inverted horizontal S-shaped member, each distal intermediate section of each non-inverted horizontal S-shaped member pulls on a proximal end of another adjacent inverted horizontal S-shaped member, each proximal intermediate section of each inverted horizontal S-shaped member pulls on the distal end of an adjacent non-inverted horizontal S-shaped member, and each distal intermediate section of each inverted S-shaped member pulls on the proximal end of an adjacent non-inverted horizontal S-shaped member thereby causing the "cells" of the S-shaped member, "nest" and cause the tubular member to attain the small diameter.

In accordance with another aspect of the present invention, the skeletal tubular member includes at least two proximal legs which are attached to the skeletal tubular member and which extend generally parallel to the longitudinal axis of the tubular member. At least one of the proximal legs includes a T-shaped flange adjacent to the end of the proximal leg for attachment to a stent release mechanism.

In accordance with another aspect of the present invention, the legs are biased outwardly away from the longitudinal axis of the skeletal tubular member. The legs may also include radiopaque markers for providing an indication of the location of the stent device as the device is positioned within a vessel.

In accordance with still another aspect of the present invention, the skeletal tubular member may include distal legs which are attached to and extend generally parallel to the longitudinal axis of the skeletal tubular member. These legs may also include radiopaque markers for providing positioning information.

In accordance with still another aspect of the present invention there is provided a self-expanding stent device which includes a small diameter skeletal tubular member. The wall of the skeletal tubular member is comprised of a plurality of cells which are formed by interconnected sinusoidal members. The sinusoidal members are generally parallel to the longitudinal axis of the tubular member. Each sinusoidal member extends for one and a half sinusoidal periods, or about 540 degrees. Each sinusoidal member has a proximal end, a distal end, a proximal peak and a distal peak. The sinusoidal members have a repeating pattern in which the proximal end of each sinusoidal member is attached to the distal peak of an adjacent sinusoidal member. Also, the distal end of each sinusoidal member is attached to the proximal peak of another adjacent sinusoidal member.

In accordance with another aspect of the present invention, in its compressed state, the proximal peak of each sinusoidal member pulls the distal end of an adjacent sinusoidal member and the distal peak of each sinusoidal member pulls the proximal end of an adjacent sinusoidal member causing the cells of the wall to collapse, or "nest," thereby allowing the skeletal tubular member to attain a small compressed diameter.

In accordance with still another aspect of the present invention, a self-expanding aneurysm cover is provided which when placed across an aneurysm of a blood vessel reduces, or obstructs, the flow of blood between the aneurysm and its related blood vessel. The aneurysm cover includes a small diameter skeletal tubular member which is comprised of a plurality of cells which are formed by a plurality of interconnected, non-inverted horizontal and inverted horizontal S-shaped members. The S-shaped members are generally parallel to the longitudinal axis of the tubular member and are interconnected in a repeating pattern. Each of the S-shaped members has a proximal end, a distal end, a proximal intermediate section and a distal intermediate section. The proximal end of each non-inverted horizontal S-shaped member is attached to the distal intermediate section of an adjacent inverted horizontal S-shaped member, the distal end of each non-inverted horizontal S-shaped member is attached to the proximal intermediate section of another adjacent inverted horizontal S-shaped member, the proximal end of each inverted horizontal S-shaped member is attached to the distal intermediate section of an adjacent non-inverted horizontal S-shaped member, and the distal end of each inverted horizontal S-shaped member is attached to said proximal intermediate section of another adjacent non-inverted horizontal S-shaped member. With this configuration, the skeletal tubular member may be compressed to a very small diameter because of "nesting" of adjacent S-shaped members.

These and other aspects of the invention and the advantages thereof will be clearly understood from the following description and drawings of a preferred embodiment of the present invention.

DESCRIPTION OF THE PREFERRED EMBODIMENT

Figure 1:
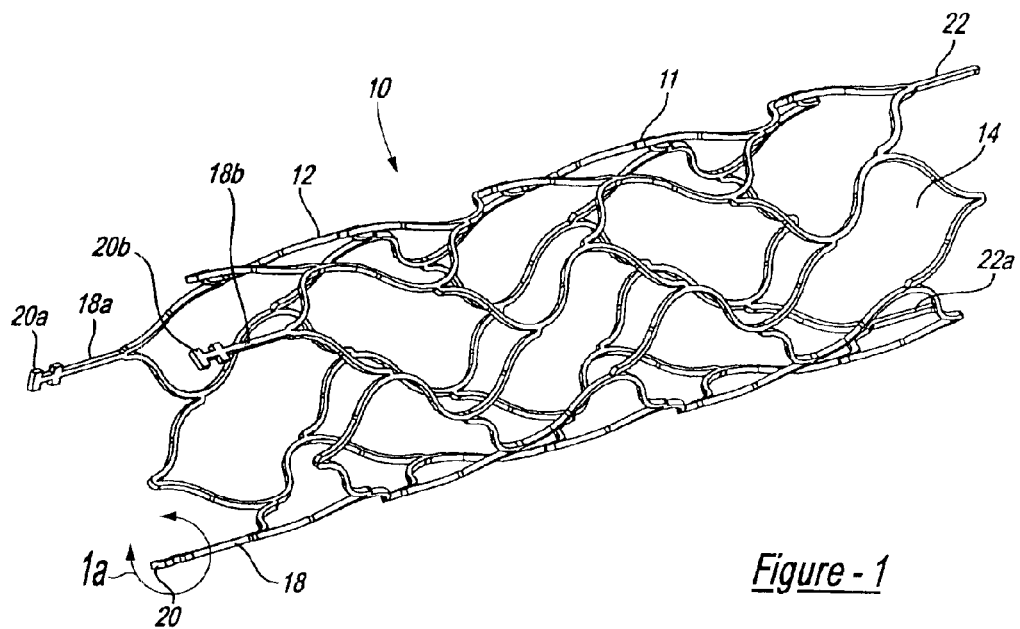
FIG. 1 is an oblique prospective view of an intravascular stent constructed in accordance with a preferred embodiment of the present invention.

FIG. 1 illustrates a self-expanding stent device 10 which is laser cut to form a thin-walled, skeletal tubular member 11 comprised of nickel-titanium alloy. Once cut, the wall 12 of the tubular member 11 includes several openings, or cells 14. When the skeletal tubular member 11 is placed over an aneurysm, a physician is able to deliver embolic coils or other such devices through the cells 14 and into the aneurysm. The tubular member 11 also functions to cover the mouth of the aneurysm thus obstructing, or partially obstructing, the flow of blood into the aneurysm. Also, the tubular member 11 prevents medical devices such as embolic coils from escaping the aneurysm.

The preferred length of the skeletal tubular member 11 may range from 0.0795 inches to 3.15 inches. The diameter of the tubular member 11 varies depending on its deployment configuration. In a non-deployed or expanded state, the diameter of the tubular member 11 may extend up to about 0.4 inches. When the skeletal tubular member 11 is compressed to fit within the lumen of a deployment catheter, the diameter may be reduced to about 0.014 inches.

Attached to the proximal end 16 of the skeletal tubular member 11 are three proximal legs 18, 18a, and 18b that extend longitudinally from the tubular member 11. The proximal legs 18, 18a, and 18b are preferably biased outwardly from the longitudinal axis of the tubular member 11. This outwardly biased configuration aids in the deployment system as subsequently described.

Figure 1A:
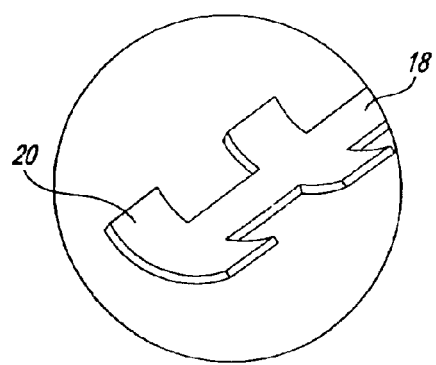
FIG. 1a is an expanded view of the proximal portion of the retaining legs shown in FIG. 1.

T-shaped or I-shaped attachment flanges 20, 20a, and 20b are attached to the tips of each proximal leg 18, 18a, and 18b. FIG. 1a describes the T-shaped or I-shaped flanges 20, 20a, and 20b in more detail. Attached to the distal end 21 of the skeletal tubular member 11 are two distal legs 22 and 22a that extend longitudinally away from the tubular member 11.

FIG. 1a illustrates in detail one of the T-shaped or I-shaped attachment flanges 20 which is also laser cut from the skeletal tubular member 11 at the proximal end of one of the proximal legs 18. The T-shaped or I-shaped attachment flange 20 is slightly arched and oriented on the proximal leg 18 such that the arch coincides with the wall 12 of the tubular member 11.

Figure 2:
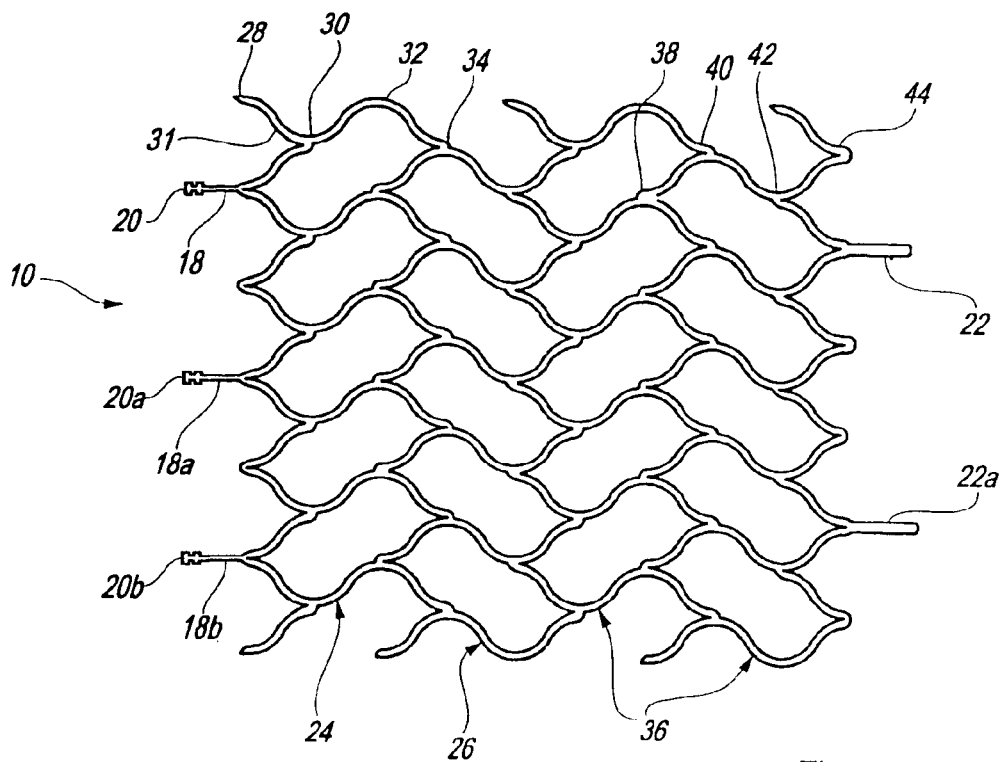
FIG. 2 is a side elevational view of the intravascular stent illustrated in FIG. 1 with the tubular stent being cut along a line and flattened into a single plane; and, FIG. 3 illustrates in more detail the proximal retaining legs of FIG. 1a and the interconnecting elements between the intravascular stent and a positioning catheter.

FIG. 2 illustrates the repetitive cell pattern of the skeletal tubular member 11. The cell pattern may be formed by interconnected non-inverted horizontal S-shaped members 24 and inverted horizontal S-shaped members 26. Each S-shaped member has a proximal end 28, a proximal intermediate section 30, a proximal portion 31, a distal intermediate section 32, and a distal end 34. The non-inverted horizontal S-shaped members 24 are slightly flattened "S" configurations laying horizontal to the axis of the skeletal tubular member 11 and having its proximal portion 31 pointing up. The inverted horizontal S-shaped members 26 are slightly flattened "S" configurations laying horizontal to the axis of the tubular member 11 and having its proximal portion 31 pointing down. The proximal end 28 is the left tip of an S-shaped member. The proximal intermediate section 30 of a non-inverted horizontal S-shaped member 24 is the negative (down) peak of an S-shaped member. The proximal intermediate section 30 of an inverted horizontal S-shaped member 26 is the positive (up) peak of an S-shaped member. The proximal portion 31 is the portion of an S-shaped member between the proximal end 28 and the proximal intermediate section 30. The distal intermediate section 32 of a non-inverted horizontal S-shaped member 24 is the positive peak of an S-shaped member. The distal intermediate section 32 of an inverted horizontal S-shaped member 26 is the negative peak of an S-shaped member. The distal end 34 is the right tip of an S-shaped member.

The S-shaped members are interconnected in a way to maximize "nesting" of the S-shaped members to thereby minimize the compressed diameter of the skeletal tubular member 11 during deployment. The proximal end 28 of each non-inverted horizontal S-shaped member 24 is connected to the distal intermediate section 32 of an adjacent inverted horizontal S-shaped member 26. The distal end 34 of each non-inverted horizontal S-shaped member 24 is connected to the proximal intermediate section 30 of another adjacent inverted horizontal S-shaped member 26. The proximal end 28 of each inverted horizontal S-shaped member 26 is connected to the distal intermediate section 32 of an adjacent non-inverted horizontal S-shaped member 24. The distal end 34 of each inverted horizontal S-shaped member 26 is connected to the proximal intermediate section 30 of another adjacent non-inverted horizontal S-shaped member 24. This interconnection of S-shaped members permits the cells 14 of the skeletal tubular member 11 to collapse and allows the tubular member 11 to attain a compressed diameter.

The cell pattern of the skeletal tubular member 11 may also be considered as being formed by interconnected sinusoidal members 36. Each sinusoidal member 36 has a period of approximately one and a half, or about 540 degrees. Each sinusoidal member 36 has a proximal end 38,. a proximal peak 40, a distal peak 42, and a distal end 44. The proximal end 38 is the left tip of a sinusoidal member 36. The proximal peak 40 is the first peak to the right of the proximal end 38 and is either positive or negative. The distal peak 42 is the second peak to the right of the proximal end 38 and is either positive or negative. However, each sinusoidal member 36 has only one positive peak and one negative peak. The distal end 44 is the right tip of a sinusoidal member 36.

The sinusoidal members 36 are interconnected in a way to maximize "nesting" of the sinusoidal members to thereby minimize the compressed diameter of the skeletal tubular member 11 during deployment. The proximal end 38 of each sinusoidal member 36 is connected to the distal peak 42 of an adjacent sinusoidal member 36. The proximal peak 40 of each sinusoidal member 36 is connected to the distal end 44 of another adjacent sinusoidal member 36. The distal peak 42 of each sinusoidal member 36 is connected to the proximal end 38 of yet another adjacent sinusoidal member 36. The distal end 44 of each sinusoidal member 36 is connected to the proximal peak 40 of still another adjacent sinusoidal member 36. This interconnection of sinusoidal members 36 permits the cells 14 of the skeletal tubular member 11 to collapse and allows the tubular member 11 to obtain a compressed diameter.

Also illustrated in FIG. 2 are the proximal legs 18, 18a, and 18b and the distal legs 22 and 22a. In the repetitive cell pattern formed by S-shaped members, the proximal legs 18, 18a, and 18b are connected to the proximal ends 28 of non-inverted horizontal S-shaped members 24 on the proximal end 16 of the skeletal tubular member 11. The distal legs 22 and 22a are connected to the distal ends 34 of inverted horizontal S-shaped members 26 on the distal end 21 of the tubular member 11. In the repetitive cell pattern formed by sinusoidal members 36, the proximal legs 18, 18a, and 18b are connected to the proximal ends 38 of sinusoidal members 36 on the proximal end 16 of the tubular member 11. The distal legs 22 and 22a are connected to the distal ends 44 of sinusoidal members 36 on the distal end 21 of the tubular member 11.

It should be understood that the stent device of the present invention may alternatively be coated with an agent, such as heparin or rapamycing, to prevent stenosis or restenosis of the vessel. Examples of such coatings are disclosed in U.S. Pat. Nos. 5,288,711; 5,516,781; 5,563,146 and 5,646,160. The disclosures in these patents are incorporated herein by reference.

Figure 3:
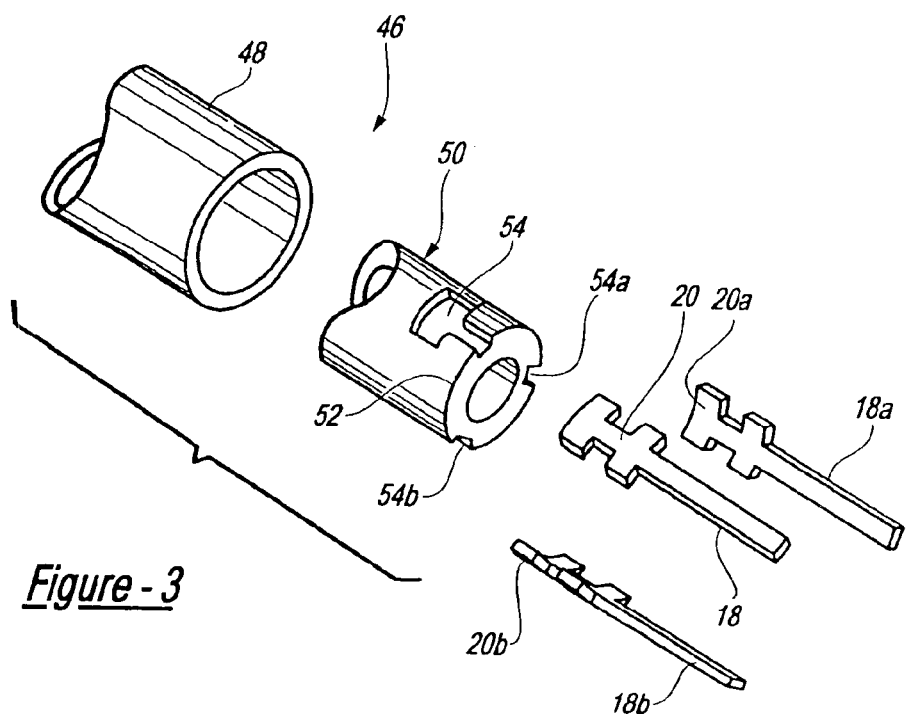

FIG. 3 illustrates the deployment system 46 for the stent device 10. The deployment system 46 includes an outer sheath 48 which is essentially an elongated tubular member, similar to ordinary guiding catheters which are well known to those of ordinary skill in the art. The deployment system 46 also includes an inner shaft 50 located coaxially within the outer sheath 48 prior to deployment. The inner shaft 50 has a distal end 52 and a proximal end (not shown). The distal end 52 of the shaft 50 has three grooves 54, 54a, and 54b disposed thereon. When the deployment system 46 is not fully deployed, the stent device 10 is located within the outer sheath 48. The T-shaped or I-shaped attachment flanges 20, 20a, and 20b on the proximal legs 18, 18a, and 18b of the tubular member 11 are set within the grooves 54, 54a, and 54b of the inner shaft 50, thereby releasably attaching the stent device 10 to the inner shaft 50. This deployment system is described in more detail in U.S. Pat. No. 6,267,783 assigned to the same assignee as the present patent application. The disclosure in this patent is incorporated herein by reference and made a part of the present patent application.

A novel system has been disclosed in which a self-expanding stent device comprises a laser cut, skeletal tubular member having a plurality of cells. Although a preferred embodiment of the invention has been described, it is to be understood that various modifications may be made by those skilled in the art without departing from the scope of the claims which follow.

What is claimed is:

1. A self-expanding stent device comprising:
   a small diameter skeletal tubular member having a thin wall and having a proximal end and a distal end; said wall of said tubular member comprised of a plurality of cells which are formed by a plurality of interconnected, non-inverted horizontal and inverted horizontal S-shaped members; said interconnected S-shaped members are generally parallel with the longitudinal axis of said tubular member; each interconnected S-shaped member has a proximal end, a distal end, a proximal intermediate section, and a distal intermediate section; and,
   said interconnected S-shaped members having a repeating pattern comprised of a configuration in which said proximal end of each non-inverted horizontal S-shaped member is attached to said distal intermediate section of an adjacent inverted horizontal S-shaped member, and said proximal end of each inverted horizontal S-shaped member is attached to said distal intermediate section of an adjacent non-inverted horizontal S-shaped member.

2. A self-expanding stent device as defined in claim 1, in which said tubular member has a small compressed diameter for delivery within a vessel and a normally biased expanded diameter for retaining said stent device against the walls of the vessel; upon compression of said tubular member to its small diameter said distal intermediate section of each non-inverted horizontal S-shaped member pulls said proximal end of another adjacent inverted horizontal S-shaped member, and said distal intermediate section of each inverted horizontal S-shaped member pulls said proximal end of another adjacent non-inverted horizontal S-shaped member thereby causing said cells of said wall to collapse and cause said tubular member to attain said small diameter.

3. A self-expanding stent device as defined in claim 1, wherein said tubular member includes a proximal leg; said proximal leg extends generally parallel to the longitudinal axis of said tubular member and is attached to the proximal end of said tubular member; the proximal leg includes an attachment flange.

4. A self-expanding stent device as defined in claim 3, wherein said proximal leg is biased outwardly from the longitudinal axis of said tubular member.

5. A self-expanding stent device as defined in claim 2, wherein said stent device is constructed from a nickel-titanium alloy.

6. A self-expanding stent device as defined in claim 3, wherein said proximal leg includes a radiopaque marker.

7. A self-expanding stent device as defined in claim 1, wherein said tubular member includes at least one distal leg; said distal leg extends generally parallel to the longitudinal axis of said tubular member and is attached to the distal end of said tubular member.

8. A self-expanding stent device as defined in claim 7, wherein said distal leg includes a radiopaque marker.

* * * * *